United States Patent [19]
Scheib et al.

[11] Patent Number: 5,628,321
[45] Date of Patent: May 13, 1997

[54] PROCESSING VELOCITY INFORMATION IN AN ULTRASONIC SYSTEM

[75] Inventors: John P. Scheib, Santa Clara; Sheng-Tz Lin, Cupertino, both of Calif.

[73] Assignee: Diasonics Ultrasound, Inc., Santa Clara, Calif.

[21] Appl. No.: 573,698

[22] Filed: Dec. 18, 1995

[51] Int. Cl.$^6$ .................................................. A61B 8/00
[52] U.S. Cl. ........................................................ 128/661.08
[58] Field of Search ........................ 128/661.08, 661.09, 128/661.1, 662.01; 73/861.18, 861.25

[56] References Cited

U.S. PATENT DOCUMENTS

| | | | |
|---|---|---|---|
| 5,139,020 | 8/1992 | Koestner et al. | 128/661.1 |
| 5,409,010 | 4/1995 | Beach et al. | 128/661.09 |
| 5,462,059 | 10/1995 | Ferrara et al. | 128/661.09 |

*Primary Examiner*—George Manuel
*Attorney, Agent, or Firm*—Blakely, Sokoloff, Taylor & Zafman

[57] ABSTRACT

A method and apparatus in an ultrasonic system for determining an optimum cardiac cycle of a living subject, and for performing vascular measurements. Peak velocities of a spectra of echoes over a period of time due to pulses emitted into a subject under examination are determined. Based upon the peak velocities of the spectra over the period of time, a time series of the peak velocities are determined representing an optimum cardiac cycle. In addition, vascular measurements of the peak velocities for the optimum cardiac cycle can be determined from the optimum cardiac cycle. The peak velocities of the spectra can be performed by dividing the spectra in a plurality of regions according to ranges of the velocity information. A threshold magnitude of the peak velocities is determined by adding a predetermined value to a minimum magnitude. The threshold magnitude is used to find a peak velocity by searching for the peak velocity from a Nyquist velocity of the spectra, identifying a first velocity which has an magnitude exceeding the threshold magnitude, and using the first velocity as the peak velocity. Determining the optimum cardiac cycle of the living subject includes setting a threshold velocity identifying each the peak velocities which exceed the threshold to form a set of candidate peak velocities. Discontinuities in the set of candidate peak velocities are determined, and the optimum cardiac cycle can be determined therefrom. Various vascular measurements for the optimum cardiac cycle include the peak systole (PS) end diastole (ED), include a minimum diastolic deflection (MDD), a rise time, an acceleration index, a pulsatility index, or a resistivity index.

76 Claims, 12 Drawing Sheets

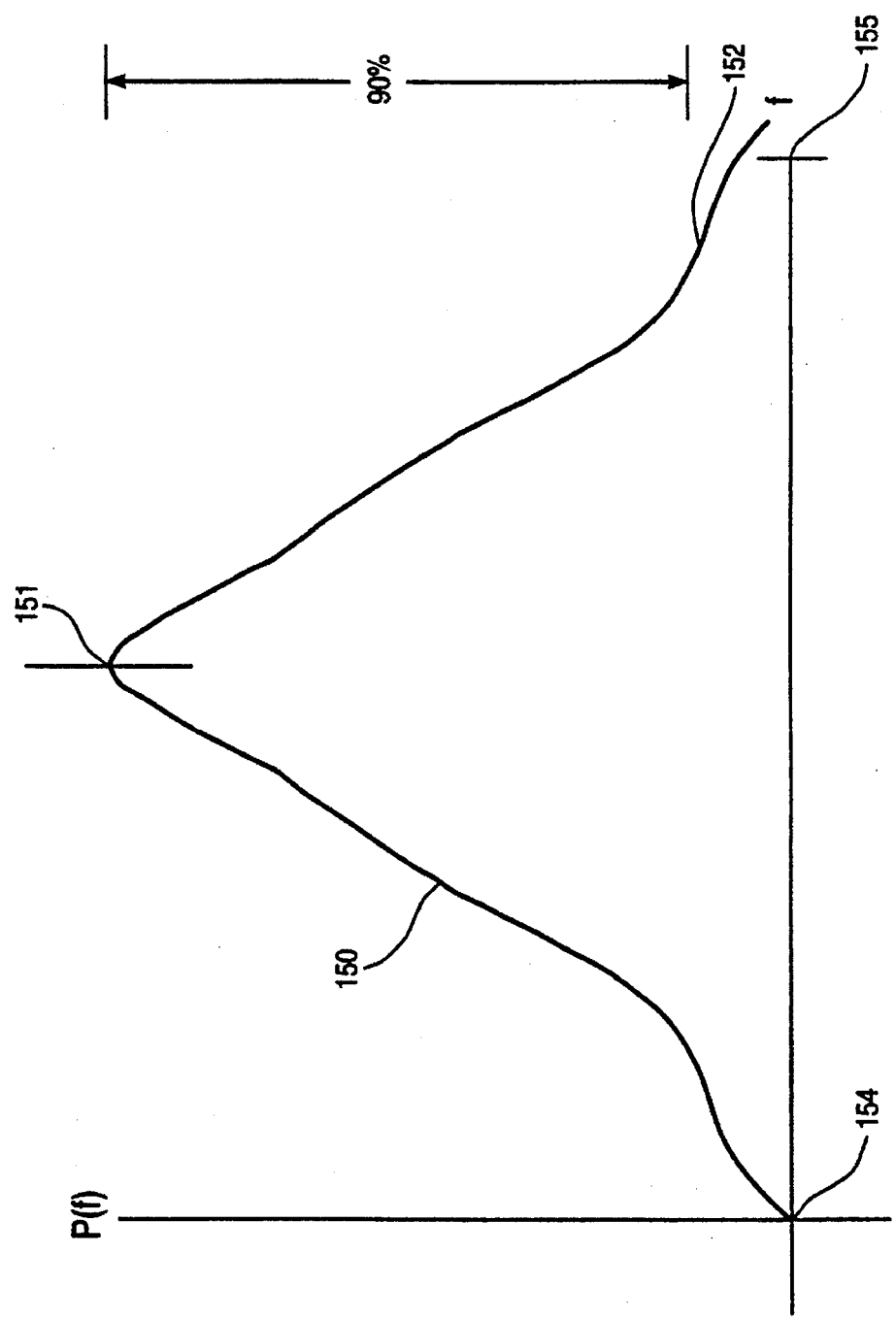
FIG_1 (PRIOR ART)

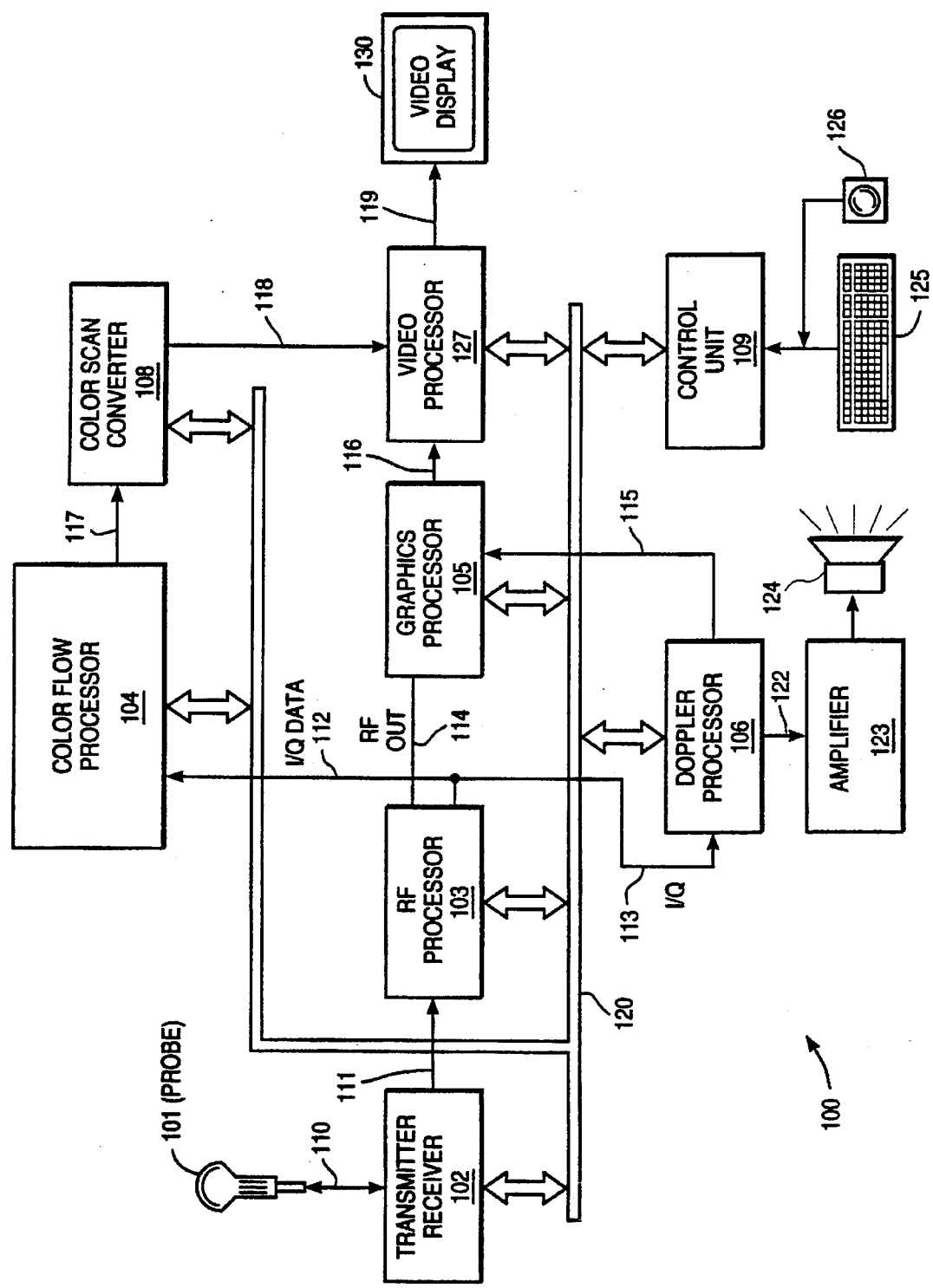

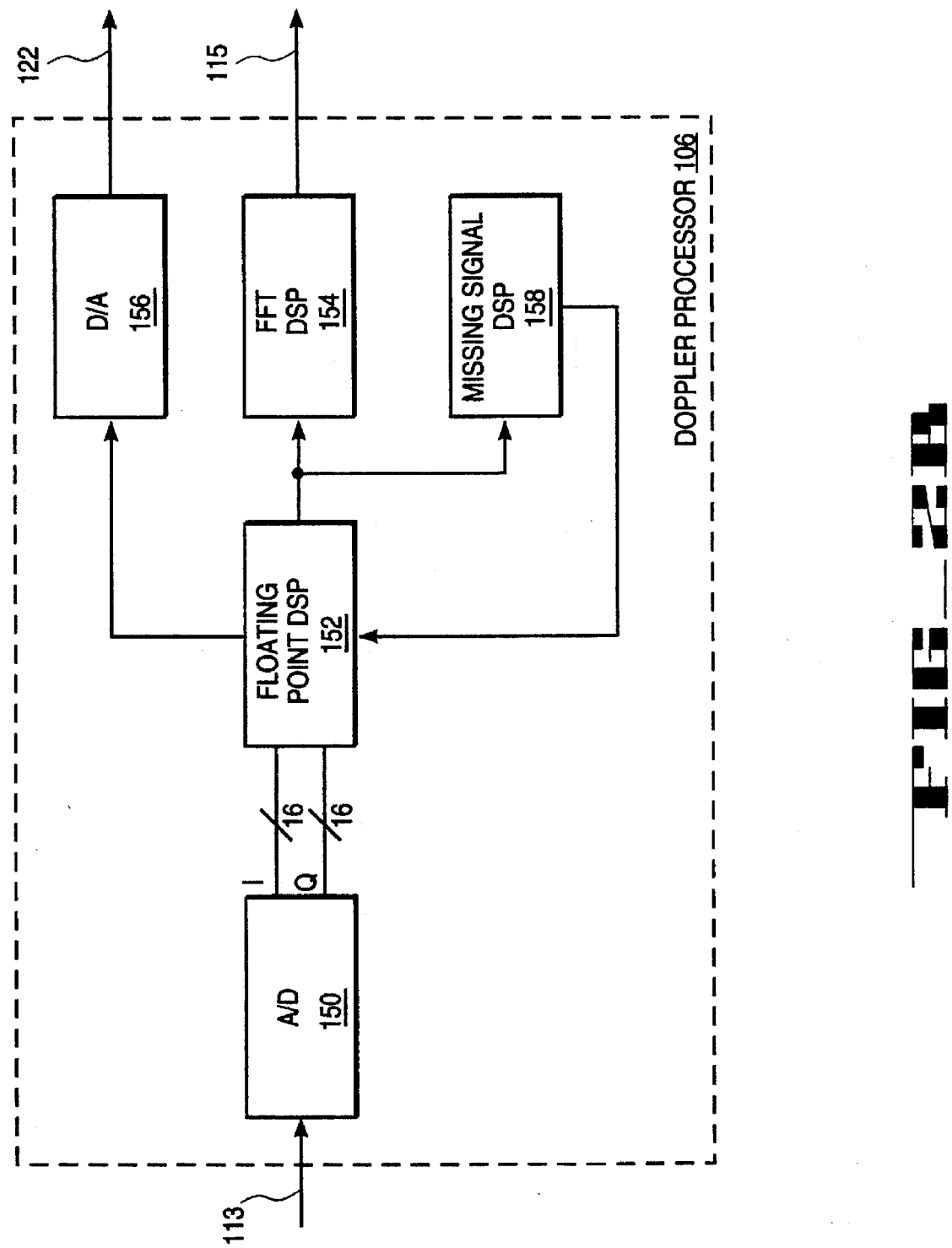

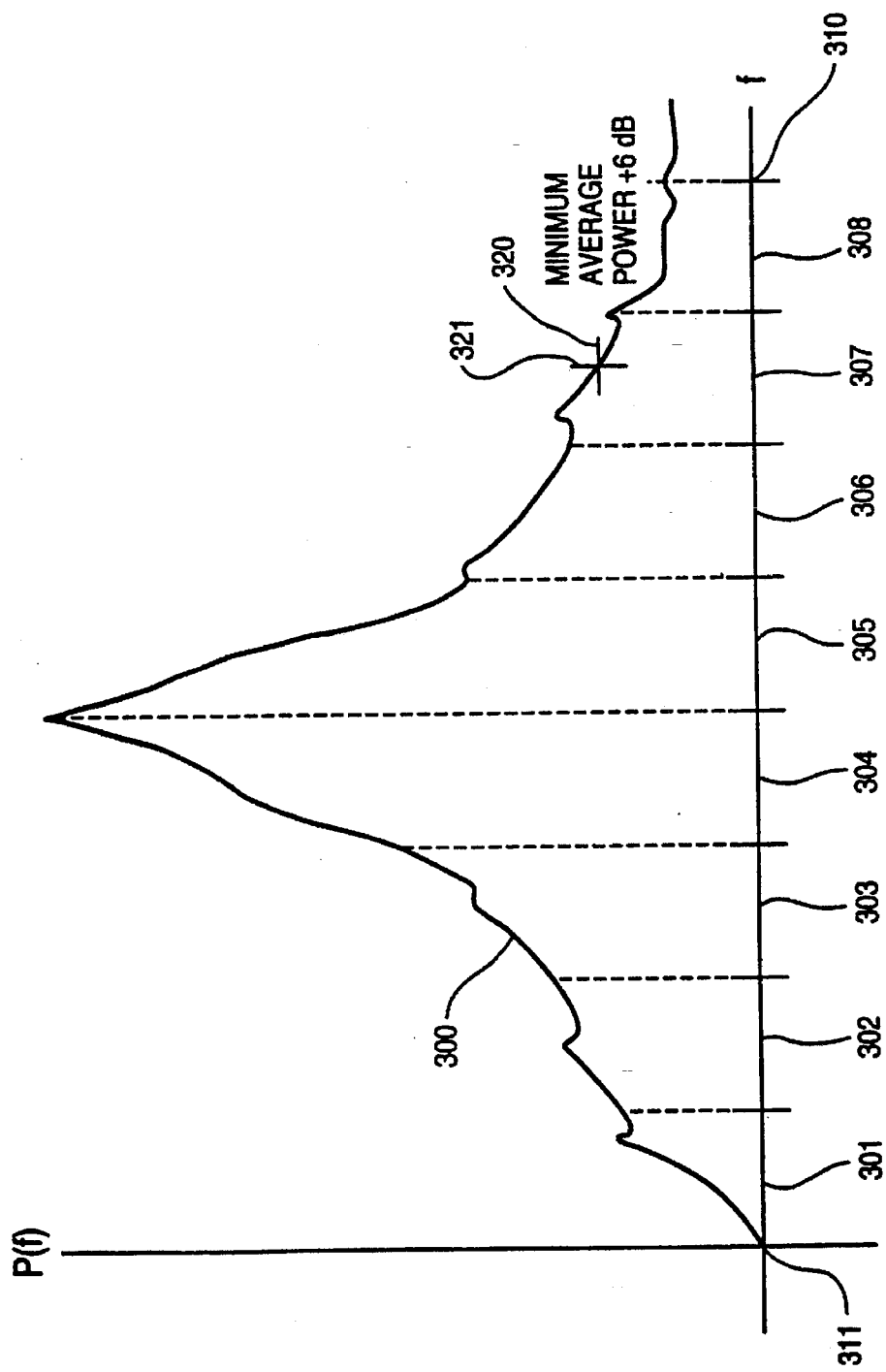
FIG_3

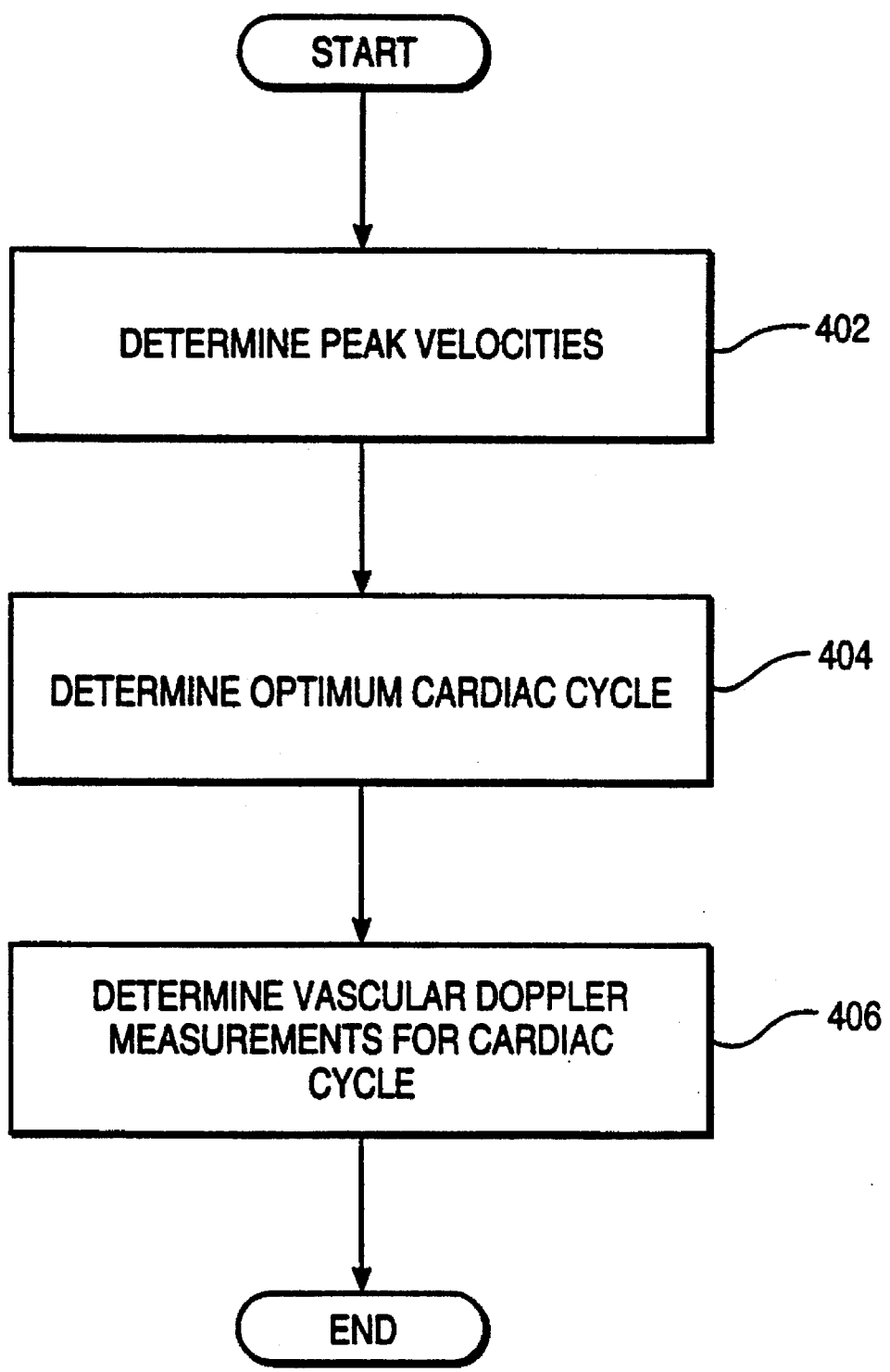
FIG_4

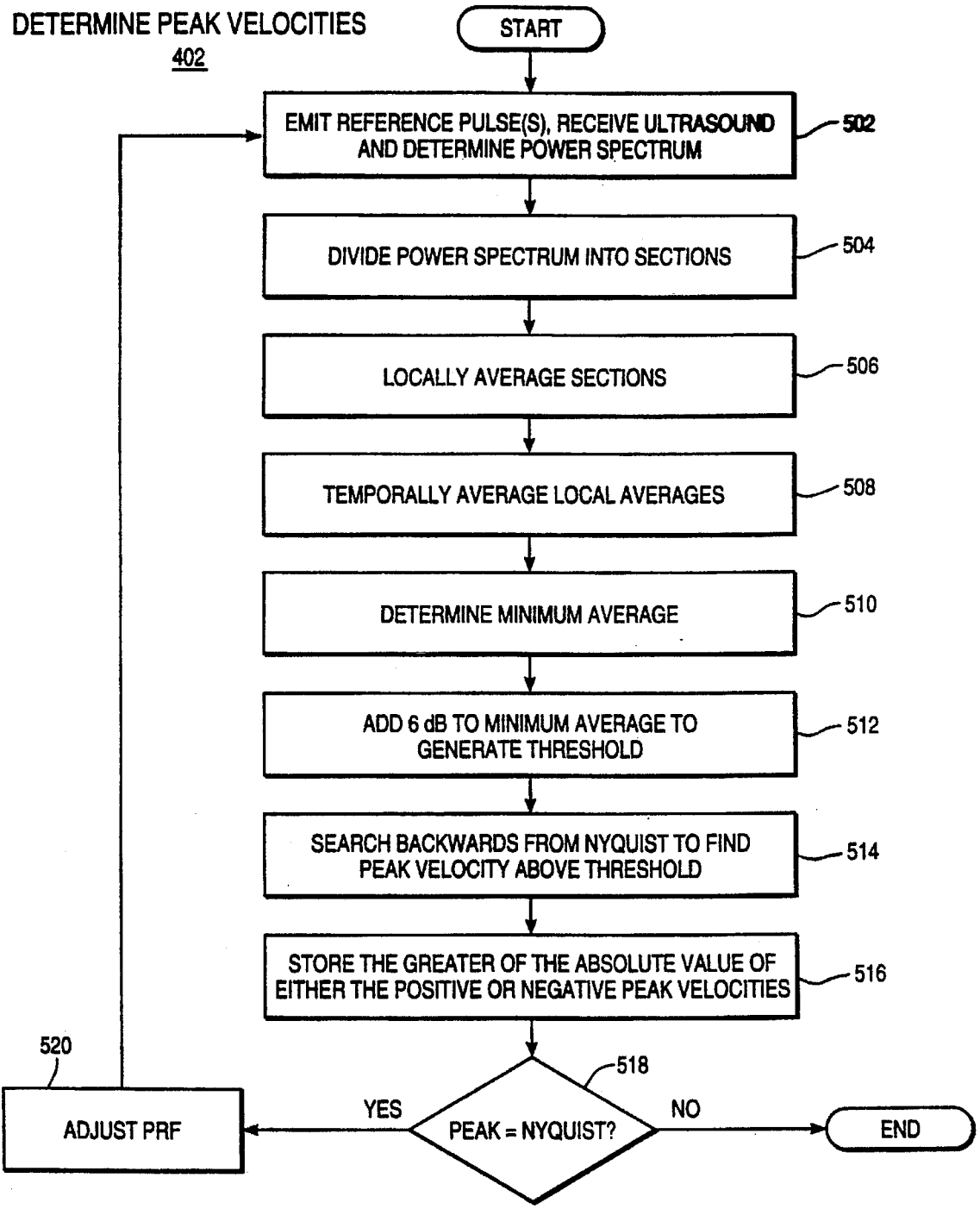
FIG_5A

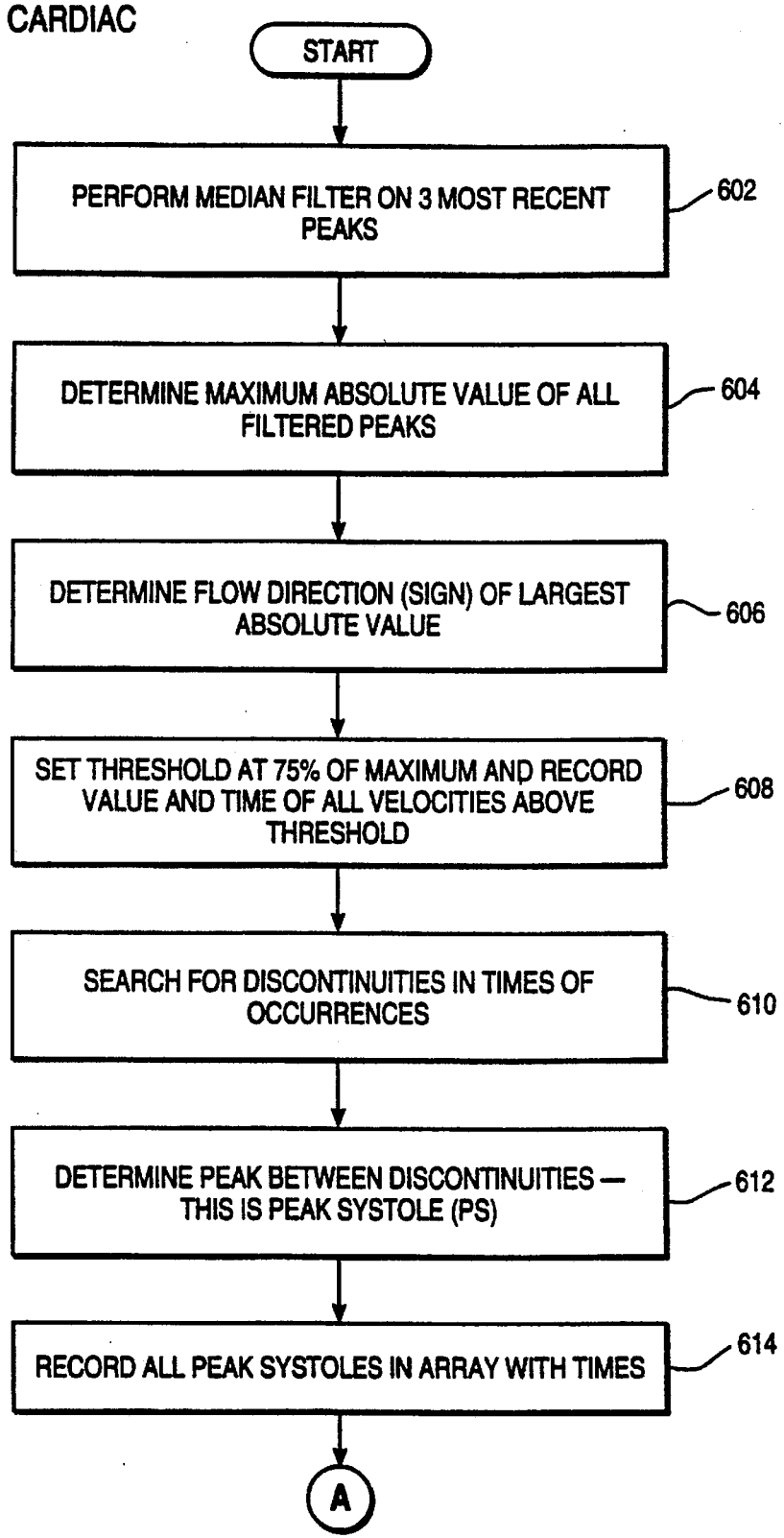

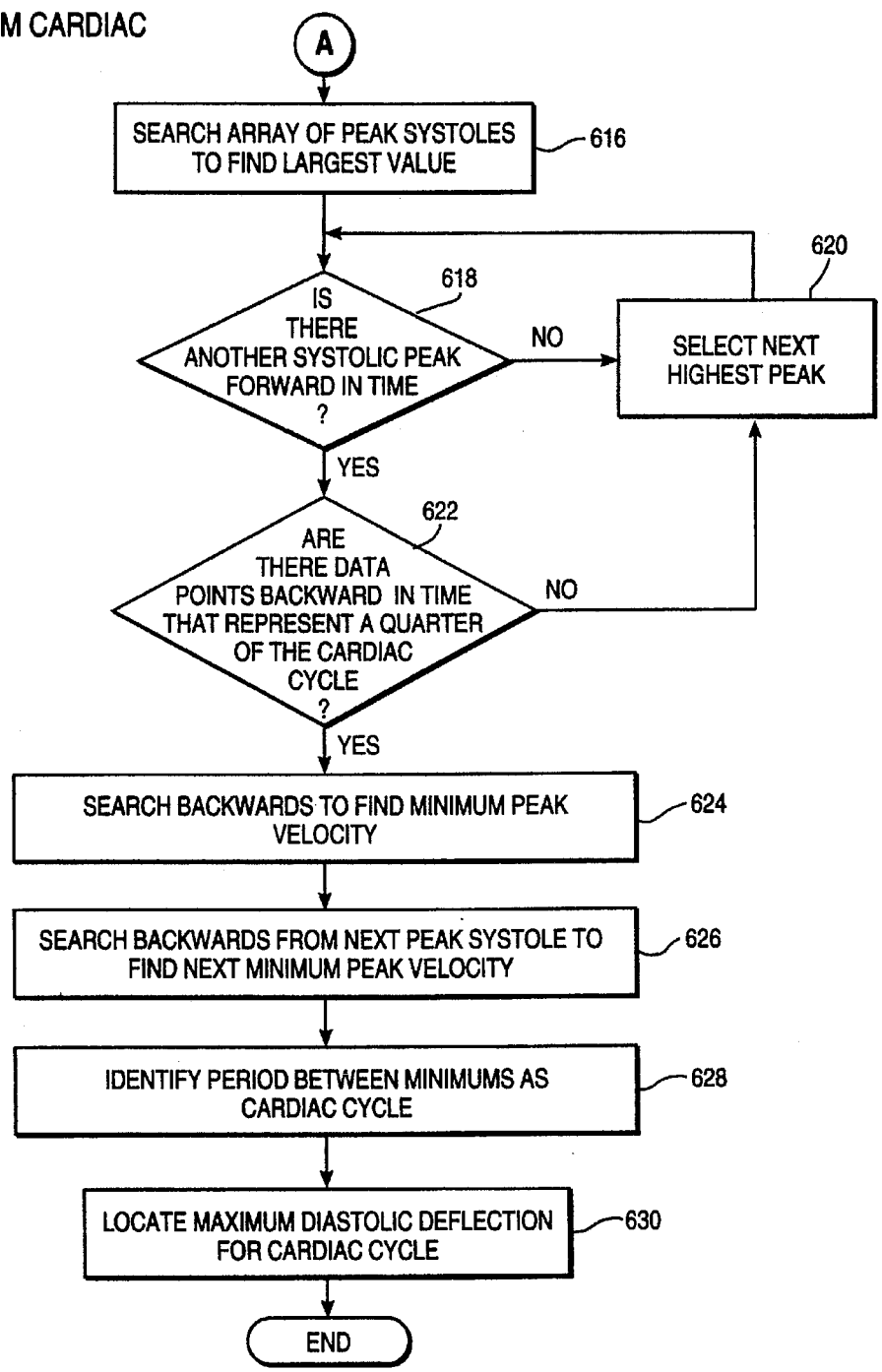
FIG_6B

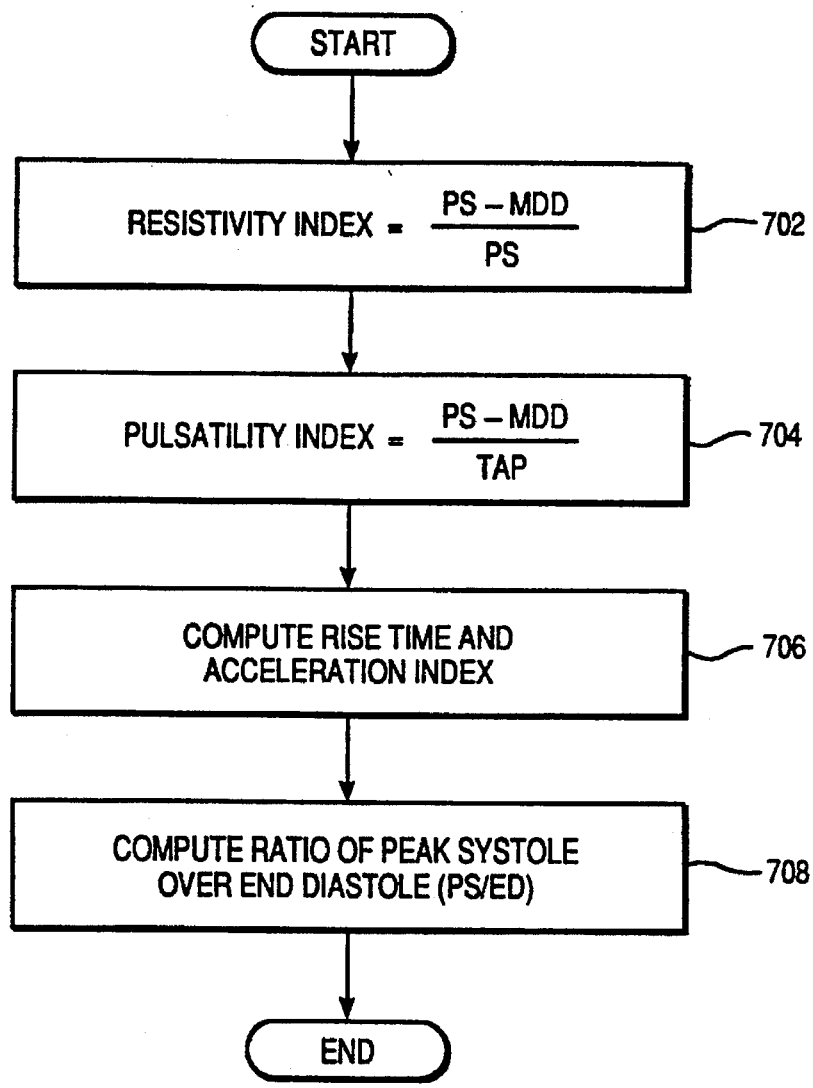
FIG_7

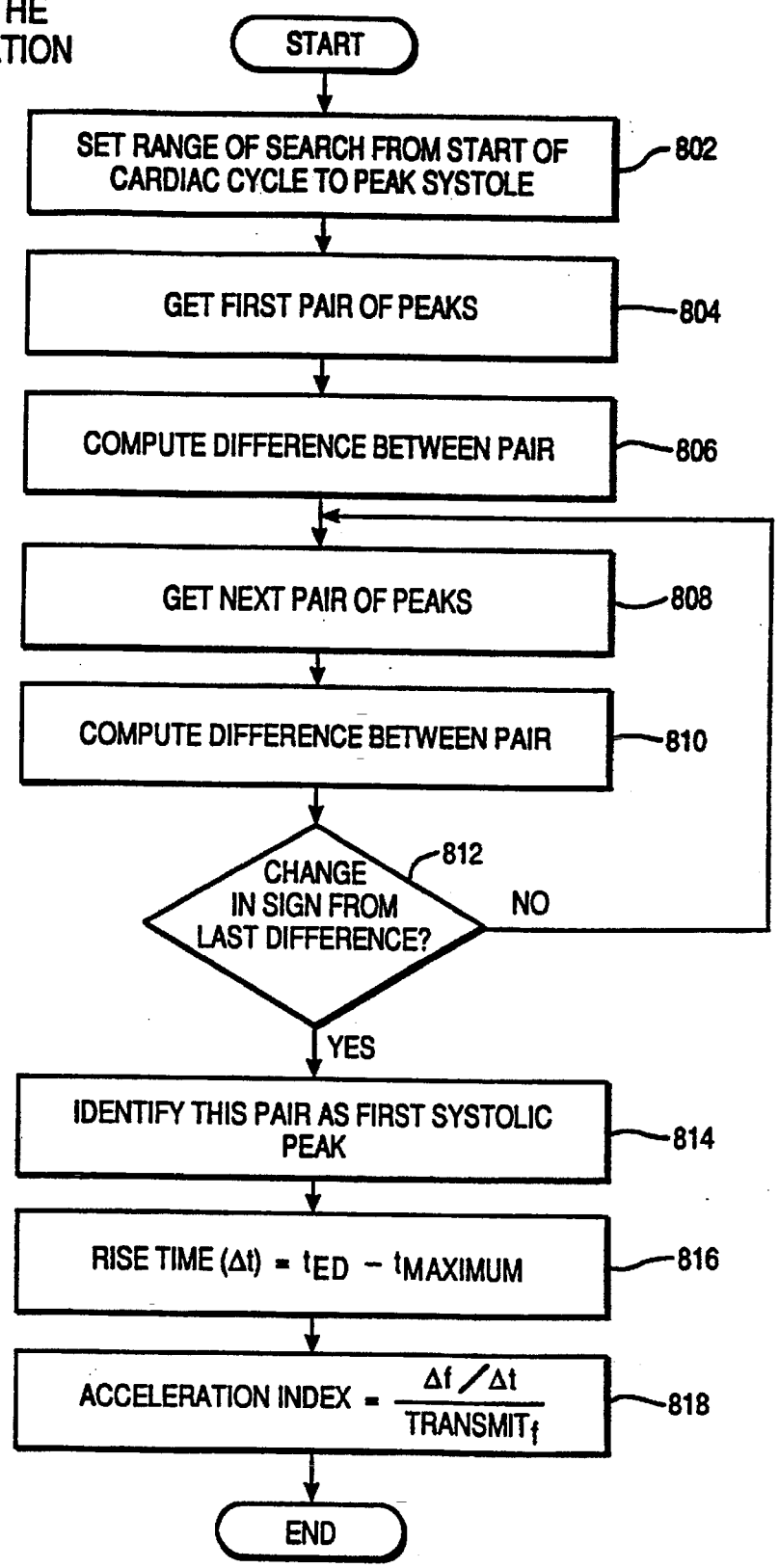
FIG_8

PROCESSING VELOCITY INFORMATION IN AN ULTRASONIC SYSTEM

BACKGROUND OF THE INVENTION

1. Field of the Invention

The present invention relates to ultrasonic imaging. More specifically, the present invention relates to a method and apparatus for determining vascular measurements of a subject in an ultrasonic system.

2. Background Information

Doppler ultrasonic imaging has been used in the medical industry to diagnose a wide variety of vascular and cardiac diseases. Due to the nature of these pathologies, vascular measurements over a cardiac cycle are important. One of these measurements is typically the value of the peak velocity of the blood flow during diastole. This measurement is made on a time average spectra of the Doppler signal. If a distribution of velocities of blood is assumed to be Gaussian, then the peak velocity will not be the same as the mean velocity and will have a considerably lower magnitude than the mean or modal velocity. Prior art ultrasound devices typically require operator intervention to mark the peak velocity. This is done usually with a graphic-type cursor that is manually positioned on the visually determined peak on a display of the system. This prior art method has two shortcomings: it is entirely dependent upon the operator, which is subject to error; and it is time consuming.

One prior art automatic method of determining peak velocities is using a fixed magnitude or power threshold to compare power spectral densities and determine the peak velocity. This threshold will be determined empirically for each probe in certain prior art ultrasound imaging apparatus, and specific gain setting used with the probe. Other prior art techniques used a statistical method to estimate a threshold based upon the power of the mean velocity. Both of these prior art methods were neither very accurate nor very robust.

For example, one prior art method of determining peak velocities operated in a manner as illustrated with reference to FIG. 1. Plot 150 of FIG. 1 illustrates a frequency shift (or velocity) versus power spectra of the received ultrasound in a Doppler ultrasonic imaging system. As can be observed, the plot 150 approximates a Gaussian distribution wherein the lowest power the signal is observed near the origin 154, and near Nyquist 155. In this prior art method, it is determined the peak power for the spectra. Then, the system assumes that 90% of the range in magnitude from 0 to the peak 151 exceeds the noise floor of the system. Thus, the velocity that is 90% of the range in magnitude from the peak magnitude is identified to be the peak velocity. This is illustrated as velocity 152 on the spectra 150 of FIG. 1.

Prior art methods, such as the peak velocity detection method above, suffer from the shortcoming that modern Doppler ultrasound systems have better sensitivity and better accuracy than those in the prior art. Thus, new adaptive techniques to determine vascular measurements are required, which exploit the sensitivity of modern ultrasound systems.

SUMMARY OF THE INVENTION

A method and apparatus in an ultrasonic system. In some embodiments, these include determining an optimum cardiac cycle of the living subject. In other embodiments, these include those for making vascular measurements from the optimum cardiac cycle. Peak velocities of a spectra of echoes over a period of time due to pulses emitted into a subject under examination are determined. Based upon the peak velocities of the spectra over the period of time, a time series of the peak velocities are determined representing an optimum cardiac cycle. In addition, vascular measurements of the peak velocities for the optimum cardiac cycle can be determined. This may be useful, for example, in a system in which the spectra are obtained by emitting the pulses into the subject under examination, receiving the echoes and determining Doppler frequency shifts from the pulses, and translating the Doppler frequency shifts to velocity information.

In a first embodiment of the present invention, the peak velocities of the spectra can be performed by dividing the spectra in a plurality of regions according to ranges of the velocity information. An average magnitude of the velocity information for each of the plurality of regions can be determined. A minimum magnitude of the average magnitudes for the plurality of regions is determined. A threshold magnitude of the peak velocities is determined by adding a predetermined value to the minimum magnitude. Then, the threshold magnitude is used to find a peak velocity by searching for the peak velocity from a Nyquist velocity of the spectra, identifying a first velocity which has an magnitude exceeding the threshold magnitude, and using the first velocity as the peak velocity. In one implementation, the steps are performed on positive and negative velocities of the spectra, determining a positive peak velocity, and a negative peak velocity, determining a greater absolute value of either the positive or the negative peak velocity and using the greater absolute value as the peak velocity.

Also, in different implementations, the values used may be those processed in a Doppler processor, or display values stored in a video memory of the ultrasonic system. The values may also be temporally averaged over a several cardiac cycles of the subject.

Determining the optimum cardiac cycle of the living subject may include setting a threshold velocity and identifying each the peak velocity which exceeds the threshold to form a set of candidate peak velocities. Discontinuities in the set of candidate peak velocities are determined, and a candidate peak velocity between each of the discontinuities is searched to form a set of peak systoles. A largest velocity of the set of peak systoles is searched to determine a candidate peak systole. It is determined whether there is a second peak systole forward in time from the candidate peak systole, and if not, a next largest velocity of the peak systoles is selected as the candidate until there is a second peak systole forward in time from the candidate peak systole. Once determined, a first minimum velocity which occurs before the candidate peak systole is identified as an end diastole (ED) for the optimum cardiac cycle. A second minimum velocity which occurs before the second peak systole is identified as a second end diastole (ED). The time period between the end diastole and the second end diastole is identified as the optimum cardiac cycle.

Various vascular measurements for the optimum cardiac cycle, including the peak systole (PS) and end diastole (IED) already determined, include a minimum diastolic deflection (MDD), a rise time, an acceleration index, a pulsatility index, or a resistivity index.

In one implementation, the rise time for the optimum cardiac cycle can be determined by successively determining differences between pairs of adjacent peak velocities between the end diastole and the peak systole, and upon detecting a sign change between a first difference and a second difference, identifying a first adjacent peak velocity as a first systolic peak velocity for the optimum cardiac cycle. The rise time for the optimum cardiac cycle is the difference in time between the first systolic peak velocity and the previous end diastole. An acceleration index for the optimum cardiac cycle can be arrived at by determining a difference between the first systolic peak velocity and the previous end diastole divided by a difference in time between the first systolic peak velocity and the end diastole.

All of the above can be performed in an ultrasonic system without user intervention, such as the identification of a cardiac cycle in a moving window on an ultrasound system's display, identify peak velocity values, or other measurements, as in certain prior art implementations.

Other objects, features and advantages of the present invention will be apparent from the description and figures which follow below.

BRIEF DESCRIPTION OF THE DRAWINGS

The present invention is illustrated by way of example and not limitation in the figures of the accompanying in which like references indicate like elements and in which:

FIG. 1 illustrates a prior art technique of determining peak velocity in an ultrasonic system with reference to a velocity versus power plot of spectra.

FIG. 2a and 2b illustrate a block diagram of an ultrasonic system in which embodiments of the present invention may be implemented.

FIG. 3 illustrates a plot of spectra of frequency shifts (velocity) versus power of received ultrasound in an ultrasonic system.

FIG. 4 is a flowchart of a method performed in an ultrasonic system in implementations of the present invention.

FIG. 5a is a flowchart of a method used for determining peak velocities.

FIGS. 6a–6b show flowcharts of a method used for determining an optimum cardiac cycle.

FIG. 7 is a flowchart of a method used for performing vascular measurements of a cardiac cycle.

FIG. 8 shows a flowchart of a method used for determining the rise time and acceleration index of a cardiac cycle.

DETAILED DESCRIPTION

Figure 5B:
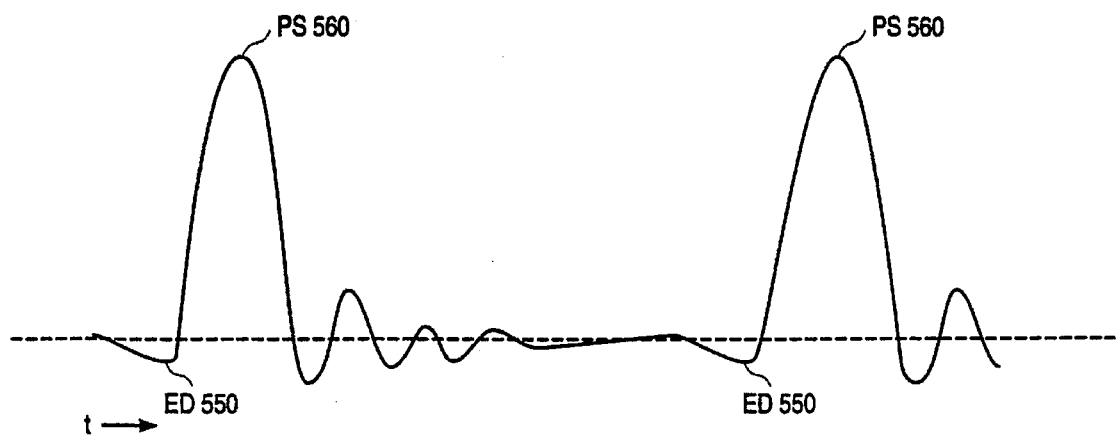
FIGS. 5b–5e are illustrations of different vascular measurements which are determined for a cardiac cycle.

The present invention is related to a method and apparatus for the performance of vascular measurements including peak velocities in an ultrasonic system. Although the present invention will be described with reference to certain specific embodiments such as certain specific hardware components, signals, processes, etc., in order to provide a thorough understanding of the present invention, it will be obvious, however, to one skilled in the art that these specific details may not be required to practice the instant invention. In other circumstances, well known components have not been described in detail in order to not unnecessarily obscure the present invention.

ULTRASONIC SYSTEM

An ultrasonic system in which embodiments of the present invention may be implemented is illustrated as system 100 of FIG. 2a. One such apparatus used in displaying information obtained from ultrasonic pulses transmitted in the human body is shown in FIG. 2a as imaging system 100. Imaging system 100 generally comprises a probe 101 which is coupled via line 110 to transmitter/receiver circuitry 102. Transmitter/receiver circuitry 102 is designed so that the elements in probe 101 will be fired at specified time intervals, with reflective pulses being detected using probe 101 at another given time interval. Transmitter/receiver circuitry 102 is coupled to control unit 109 via bus 120. Control unit (or host computer) 109 controls all circuitry in the imaging system via bus 120. Control unit 109 is further coupled to a keyboard 125 and a mouse, trackball or other device 126 for movement and control of information shown on video display 130.

Once a pulse is received by transmitter/receiver 102, such information is transmitted by line 111 to RF (radio frequency) processor 103 for further processing. This radio frequency information is further transmitted via line 114 to a graphics processor 105 and to a Doppler processor 106 via lines 114 and 113 for generation of black and white ultrasound information on video display 130. Information generated by Doppler processor 106 via in-phase (I) and quadrature (Q) signals output from RF processor 103 are transmitted via line 115 to graphics processor 105. Graphics processor 105 transmits scan line information to video processor 127 via line 116.

In addition to information passed to graphics processor 105 and Doppler processor 106, RF processor 103 transmits I and Q signals via line 112 to color flow processor 104. Color flow processor 104 is also controlled by control unit 109 via bus 120. Color flow processor 104 is used for detecting Doppler shift and blood flow information in living tissue, and thus transmits this information via line 117 to a color scan converter 108. Such color information is used to graphically represent on video display 130 moving blood flow in a living organism.

The color scan converter is used to interpolate point scan line information obtained from color flow processor 104, and transmit that information on line 118 video processor 127 for representation of blood flow in the human body. Video processor 127 then uses information obtained from graphics processor 105 for display of black and white ultrasound information suitable for output on a video display such as 130 via line 119. Such information may be transmitted in National Television Standards Committee (NTSC) format and thus be stored on video tape for later clinical examination by attending medical personnel.

The methods which are to be described here may be operative either within Doppler processor 106 operating upon the raw sampled Doppler power spectrum itself, or it may be processed in the host computer 109, upon compressed data represented as a logarithmically compressed power spectrum. In either event, an improved method of peak velocity detection is provided by performing the methods and implementing the apparatus to be described here.

DOPPLER PROCESSOR

The details of Doppler processor 106 are shown in more detail in FIG. 2b. Doppler processor 106 receives input data from RF processor 103 over signal lines 113. The input data include the in-phase (I) and quadrature (Q) data which is generated by RF processor 103. Doppler processor 106 includes a front end analog to digital (A/D) converter 150 which outputs the I and Q data to floating point DSP 152. Floating point DSP 152 converts the fixed point I and Q data received from A/D converter 150 to floating point, and performs a wall filter upon the data to remove any stationary artifacts. Moreover, floating point DSP 152 performs audio processing which includes forward and reverse separation of the data. This data is then output to a digital to analog (D/A) converter 156 can be then made available to an amplifier 123 as shown in FIG. 2a. This is then output to a single or plurality of speakers 124 to output the audio data.

The wall filter contained within the floating point DSP 152 also outputs its data to the missing signal DSP 156. Missing signal DSP 156 includes an interpolation algorithm which is performed upon the interleaved data samples which are used to generate separate B-scan and Doppler data. Missing signal DSP 156 interpolates the missing points not provided to Doppler processor 106. Feedback is provided from missing signal DSP 156 to floating point DSP 152 in order that the interpolated points are provided in the incoming signal path.

Floating point DSP 152 is further coupled to a FFT DSP 154 which performs a Fast Fourier Transform on the floating point data in order to extract the requisite signal data from the input I and Q signals. In addition, FFT DSP 154 performs the temporal averaging, peak velocity detection, and other vascular processing which is described here. The output of the FFT DSP 154 provided on signal lines 115, is processed by the graphics processor 105 and retained in a display memory contained therein.

Note that in implemented embodiments, each of the digital signal processors 152, 154, or 156 include an AT&T 32C digital signal processor and any accompanying memory and control logic which is required for operation of the predetermined functions. Thus, although each of the DSP's include a small memory area for computational purposes, the algorithms performed within each of the DSP's may be loaded from a long term memory (e.g. a hard disk drive or read-only memory (ROM), or other non-volatile storage means into the volatile memory.

In either the host computer 109 or Doppler processor 106, the methods to be described here are implemented in a computer programming language such as a high-level (e.g., C or C++) or assembly programming language, converted to machine code, and loaded from long-term storage at system run-time for execution. Thus, the techniques to be described here may be implemented either as computer program which is stored in long-term storage and loaded and executed at system run-time or, alternatively, implemented in discrete hardware components such as large-scale integrated circuits (LSI's), application-specific integrated circuits (ASIC's) or in firmware such as electrically erasable programmable read-only memory (EEPROM's).

SIGNAL PROCESSING

The methods of implemented embodiments of the present invention will be described with reference to FIGS. 3 through 8. FIG. 4 illustrates the overall method performed in implemented embodiments of the present invention. Process 400 starts by identifying peak velocities at step 402 in a power spectrum obtained in the ultrasonic system 100 shown in FIG. 2a by the emission of ultrasonic pulses, the reception of echoes and the generation of the power spectrum, and determination of peak velocities of the spectrum over time. The details of this process are shown in FIG. 5a. Subsequently, the optimum cardiac cycle, based upon these peak measurements, is determined at step 404. The details of this process are shown in FIGS. 6a–6b. Then, at step 406, various vascular measurements are made over the course of the optimum cardiac cycle. This process is shown and discussed with reference to FIGS. 7–8.

PEAK VELOCITY DETECTION

As illustrated in FIG. 5a, peak velocity detection starts at step 502, reference pulses are emitted into the subject under examination in order to determine the movement of a substance within the subject and receive ultrasound, using well-known prior art techniques. In embodiments of the present invention, received ultrasound is converted into a power spectrum such as the plot 300 of FIG. 3. In Doppler processor 106, each frequency shift (or velocity) is represented as a 32-bit floating point value. Note that for the remainder of this patent application, velocity and frequency shifts may be used interchangeably, except where otherwise indicated. Thus, the reference of one may therefore refer to the other. In host computer 109, compressed data is accessed in the graphics memory in graphics processor 105 and represented as 8-bit data which represents a logarithmically compressed power spectrum. As illustrated in FIG. 3, although only a positive direction is shown in the plot 300, a negative spectrum is also generated. The plot shown in FIG. 3 illustrates a plot from an origin 311 to Nyquist 310. Note that the distribution of the spectrum is approximately Gaussian, as in a typical prior art velocity spectrum. Using the apparatus in implemented embodiments, there are 256 samples of velocity or shift values for both positive and negative directions. At step 504, the power spectrum is then divided into sections, as illustrated in FIG. 3, 8 sections 301–308 of 16 data points each. The noise floor of the system can be approximated.

At step 506, the power of each of the sections 301–308 is locally averaged. The averages determined at step 506 are then temporally averaged at step 508 in order to eliminate any temporal artifacts such as tissue flash. Once the average power has been computed for all of sections 301–308, at step 508, then a minimum average of all the averages is determined at step 510. This minimum average of the sections is then used as the noise floor of the system.

Using the minimum average of the system a pre-defined value, in this embodiment 6 dB, is added to the minimum average power in order to determine the threshold above which peak velocities will be identified. This is determined at step 512. Once the threshold has been generated, the process then proceeds to search through the spectrum starting from Nyquist 310 at step 514, to determine the peak velocity. Again, assuming a Gaussian distribution as is typical in an ultrasonic system spectrum, starting at Nyquist 310, the search proceeds from 310 towards the origin 311 in order to find the peak velocity. As illustrated, the threshold may then be established at a calculated power such as 320 illustrated in the plot of FIG. 3. Then, the velocity having the first power to exceed the threshold, as illustrated in FIG. 3, point 321, is identified as a peak velocity.

Note that steps 504–514 are also performed for the negative spectra, wherein a search is performed from the negative Nyquist toward the origin as illustrated in FIG. 3. Then, at step 516 of process 500, the greater of either of the absolute values of the positive or negative peak velocities is stored as the absolute peak velocity in the system. Then, at step 518, it is determined whether the stored peak velocity is equal to Nyquist. If so, then the PRF (pulse repetition frequency) of the system may be adjusted, as shown in step 520, and the process repeats with the adjusted PRF. If not, then the peak velocity has been determined and process 500 is complete.

As previously discussed, process 500 of FIG. 5a can be performed upon the unprocessed 32-bit I/Q data determined from the DSP's within Doppler processor 106. Note that the data has also been passed through a wall filter so that if the power in a region exceeds the value of the wall filter, then it is discarded and not used for determining the minimum average.

DETERMINING OPTIMUM CARDIAC CYCLE

The foregoing method then allows a set of vascular measurements to be made for an identified cardiac cycle. A time series of the peak velocities obtained using process 402 is obtained, and stored in Doppler processor 106 or graphics memory available to host computer 109 memory over time. This time series can then be processed to perform the vascular measurements. In certain prior art systems, both the peak measurements and the cardiac cycles were identified by clinicians operating the ultrasound system on a strip chart or other continuous system display.

As each peak measurement is obtained from process 402, this time series of peaks is then processed to determine a median temporal filter of the three most recent peak velocities. The median-filtered peaks are then stored in memory at step 602 shown in FIG. 6a. This reduces false peak velocities which may be noise. Subsequent to the obtaining of the median of the three most recent peaks, a maximum absolute value is determined by scanning all the median-filtered peaks at step 604. This value can then be used as a threshold. The value is then examined to determine the flow direction (or sign) of the maximum absolute value at step 606. The flow direction or sign is used for compensating for a negative flow direction indicating that the probe is directed differently. In this instance, all the tests are correspondingly adjusted, e.g., to search for maximum values for the vascular measurements, instead of minimum values, or vice versa. For the purposes of this application, flow direction is assumed to be positive.

A threshold is then set at step 608 which is 75% of the maximum absolute value, and the median-filtered data set is again processed to record the record the data value and time of occurrence of each value above the threshold. Step 610 then searches for discontinuities in the times of occurrences of each of the peaks above the threshold. In implemented embodiments, if there are more than 20 spectral lines (20 samples over time in the median-filtered data set) between one sample and another, then there is a discontinuity. The ultrasonic system of implemented embodiments stores approximately 400 spectral lines in a time series over a 1, 2, 4 or 8 second time period, according to an operator setting. The discontinuities represent the start and stop times of the systolic peaks of the multiple cardiac cycles of the time series.

The portions of the peak velocities bounded by these start and stop times are then searched at step 612 to find the peak velocity within each of the regions of the time series. The peak velocity within each of the time periods is then identified as a peak systole (PS). All of the peak systoles 560 as shown in FIG. 5b are stored for further processing.

As illustrated in FIG. 5b, each of the peak systoles 560 determined at step 612 of FIG. 6c is recorded into an array of peak systoles along with an accompanying time of occurrence of the peak at step 614. This minimum peak velocity which occurs before any PS value 560 is identified as the end of diastole (ED) 550 for each of the peak systoles, as shown in FIG. 5b.

Subsequent to the determination of the peak systoles (PS) and the corresponding end diastole (ED) for each, the PS having the largest value is used as a candidate PS for an optimum cardiac cycle. This value is determined at step 616 of FIG. 6b. Two criteria must be met in order for the candidate PS to be used as that for the optimum cardiac cycle. First, as detected at step 618, it is determined whether there is another peak systole which is forward in time from the candidate PS. If not, then this candidate PS is rejected and this candidate cardiac cycle is discarded as the optimum. The next highest peak systole is retrieved for such examination at step 620.

Figure 5C:
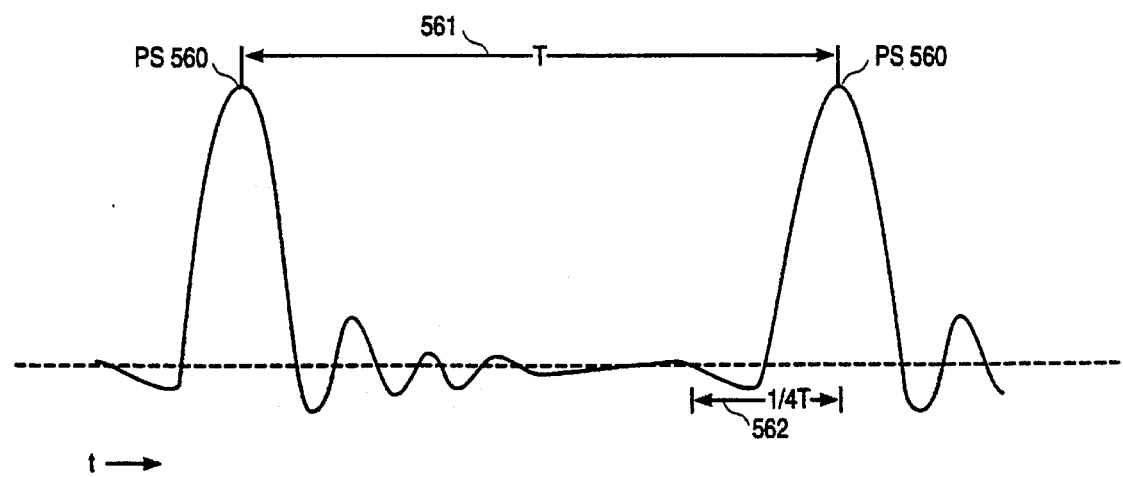

If there is another peak systole forward in time, as detected at step 618, then it is determined at step 622 whether there are data points backward in time from this peak for approximately one-fourth (¼) 562 of the period T 561 of the cardiac cycle as shown in FIG. 5c. If there are not data points for the whole range 562 of the one-fourth of the cardiac cycle before the PS value 560, then the next highest peak is selected at step 620 and used as the candidate PS for the next candidate optimum cardiac cycle. Steps 618–622 repeat until both criteria are met for the PS being examined.

Once the candidate PS has been selected as the optimum PS for the optimum cardiac cycle, the array of median-filtered peaks are then searched to find the starting and ending points of the cardiac cycle bounded by the end diastole (ED) for two adjacent cycles.

Figure 5D:
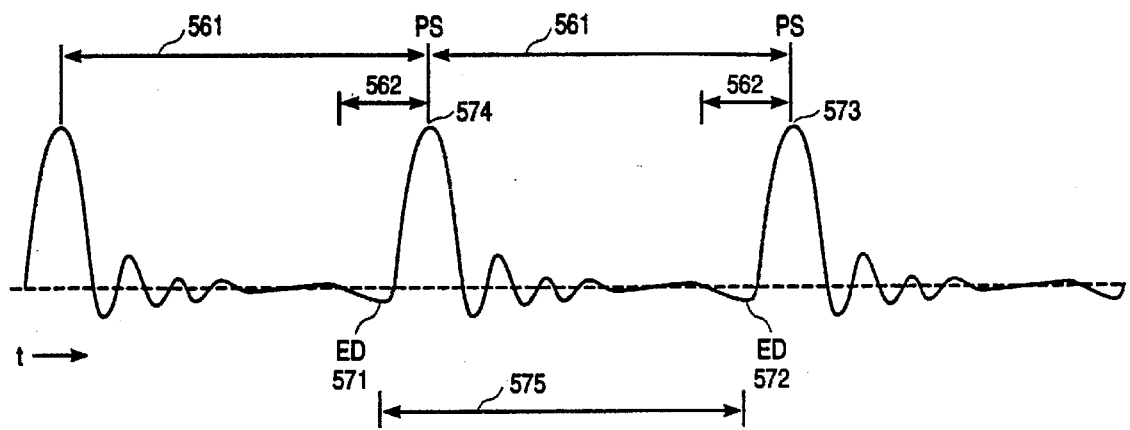
Figure 5E:
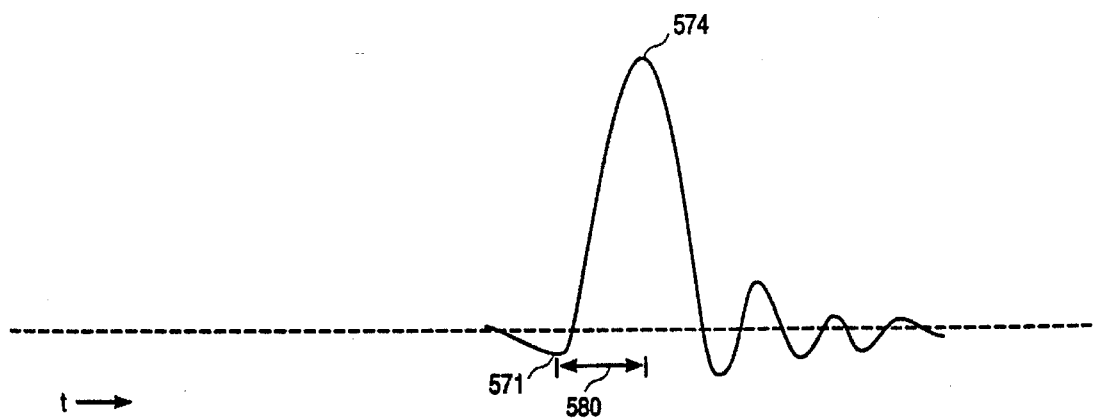

First, the array of median-filtered peak velocities are searched backwards in time from the location of the optimum PS 574 as shown in FIG. 5d to find the minimum peak velocity which occurs before PS 574 at step 624. This value is then used as the first ED term 571. The search is bounded by one-fourth 562 of the period T 561 of this optimum cardiac cycle. Subsequently thereto, at step 626, the median-filtered peaks are searched forward in time in order to find the next minimum velocity 572 which occurs before the next PS 573 forward in time from the PS 574 in the time series. At step 628 the period between the two minimum velocities 571 and 572 is then identified and stored as the optimum cardiac cycle 575 which then can be used for additional processing, such as performing vascular measurements. Subsequent thereto, the minimum diastolic deflection (MDD) term can be searched for within the cardiac cycle at step 630. In most circumstances, it is equal to or can be approximated by ED, although it can vary in other instances.

VASCULAR MEASUREMENTS

FIG. 7 illustrates the various vascular measurements which are performed using the identified optimum cardiac cycle 575 and the PS and ED values 574 and 572 determined above. Step 702 shows the calculation of the resistivity index as follows:

$$\text{resistivity\_index} = \frac{PS - ED}{PS}$$

The pulsatility index can then be calculated at step 704 as follows:

$$\text{pulsatility\_index} = \frac{PS - MDD}{TAP}$$

wherein TAP is the time averaged peak. TAP is computed at step 704 by calculating the mean of the recorded peaks within the optimum cardiac cycle.

At step 706, the rise time and acceleration index are computed. The details of this process are shown in more detail and discussed with reference to FIG. 8. Finally, step 708 illustrates the computation of the ratio of the peak systole (PS) to end diastole (PS/ED).

RISE TIME AND ACCELERATION INDEX

FIG. 8 illustrates the process 706 of determining the rise time and acceleration index in more detail. The rise time is computed as the difference of the time of the end diastole (ED) term 571 which identifies the start of the cardiac cycle and a first systolic peak thereafter. The first systolic peak is found by searching the time series of peak velocities from the start of the cardiac cycle for a local maximum. First, at step 802 as illustrated in FIG. 8, the range 580 shown in FIG. 5e of the search for the local maximum is set to the start of the cardiac cycle (ED) 571 to the peak systole (PS) 574. At step 804, the first pair of median-filtered peaks in this range of the time series are retrieved, and the difference between them is computed at step 806. The next pair of peaks in the range is then retrieved at step 808, and the difference between these is computed at step 810. It is then determined, at step 812, whether there has been a change in sign of the difference between the last difference and the current difference. If not, then the next pair is again retrieved at step 808, the current difference becomes the last difference and the loop continues. The new current difference is computed and the remaining processing is again performed.

Steps 808–812 continue until a change in sign of the difference between the pair of differences from the time series is observed. When this occurs, the first value of the current pair is defined as the local maximum. Once identified, the time of the local maximum $t_{maximum}$ can be used for computation of the rise time $\Delta t$ at step 816 by subtracting it from the time of start of the cardiac cycle tED as shown in FIG. 8. The acceleration index is also computed, as shown at step 818 in FIG. 8, as the change in frequency ($\Delta f$) between the pair divided by the change in time ($\Delta t$), as normalized by the transmit frequency (transmit$_f$) of the reference pulse(s). In contrast to the remainder of the vascular measurements in this patent application, the acceleration index uses only the frequency rather than velocity. The vascular measurements are thus complete.

Thus, using these described embodiments of the present invention, improved sensitivity over prior art methods of determining peak velocities, an optimum cardiac cycle, and performing vascular measurements without user intervention has been described. Note that the method may be performed either upon raw 32-bit data representing determined velocity (or shifts) in the Doppler processor 106 or, alternatively, may be performed upon compressed data stored in a video memory in graphics processor 105 by host computer 109. In either event, similar results may be achieved with the attendant advantages and disadvantages of using either type of dam. Note further that although the system has been described especially with reference to pulsed doppler ultrasonic systems, this may also have equal application to multiple gate ultrasonic systems, especially those used for imaging subjects such as human patients under examination. The techniques may have equal application to other fields utilizing a number of samples of frequency shifts from reference pulses, such as continuous wave (CW) doppler ultrasonic systems, or other technologies such as radar or sonar.

Thus, an improved technique for performing vascular measurements in an ultrasonic system has been described. Although the present invention has been described with reference to particular embodiments thereof, especially as illustrated in FIGS. 1–8, these should be viewed as illustrative only, and are not to be viewed as limiting the present invention. Other modifications or substitutions may be made by one skilled in the art, without departing from the overall spirit and scope of the present invention. Thus, the present invention is only to be construed as limited by the appended claims which follow.

What is claimed is:

1. A method of making vascular measurements within a living subject in an ultrasonic system comprising the following steps:
   a. determining peak velocities of a spectra of echoes over a period of time due to pulses emitted into a subject under examination, determining said peak velocities includes dividing said spectra into a plurality of regions to determine a threshold magnitude of said peak velocities and identifying a first velocity that exceeds said threshold magnitude;
   b. based upon said peak velocities of said spectra over said period of time, determining a time series of said peak velocities representing an optimum cardiac cycle for said subject under examination; and
   c. based upon said time series of said peak velocities representing said optimum cardiac cycle, performing vascular measurements of said peak velocities for said optimum cardiac cycle.

2. The method of claim 1 wherein said spectra are obtained by emitting said pulses into said subject under examination, receiving said echoes and determining Doppler frequency shifts from said pulses, and translating said Doppler frequency shifts to velocity information.

3. The method of claim 1 wherein said step of determining said peak velocities of said spectra comprises:
   a. dividing said spectra in a plurality of regions according to ranges of said velocity information;
   b. determining an average magnitude of said velocity information for each of said plurality of regions;
   c. determining a minimum magnitude of said average magnitudes for said plurality of regions;
   d. determining a threshold magnitude of said peak velocities by adding a predetermined value to said minimum magnitude; and
   e. using said threshold magnitude to find a peak velocity by searching for said peak velocity from a Nyquist velocity of said spectra, identifying a first velocity which has an magnitude exceeding said threshold magnitude, and using said first velocity as said peak velocity.

4. The method of claim 3 further comprising the step of repeating said steps a–e on positive and negative velocities of said spectra, determining a positive peak velocity, and a negative peak velocity, determining a greater absolute value of either said positive or said negative peak velocity and using said greater absolute value as said peak velocity.

5. The method of claim 3 wherein said step of determining said spectra comprises determining a Doppler spectrum, performing a wall-filter on said spectrum, and determining a power estimate of said spectrum.

6. The method of claim 3 further comprising the step of modifying a pulse repetition frequency (PRF) of said pulses if said peak velocity is at said Nyquist velocity in said spectra.

7. The method of claim 3 further comprising the step of averaging said peak velocity over several cardiac cycles of said subject under examination using said method.

8. The method of claim 3 wherein said step of determining said spectra comprises using display values for said ultrasonic system, and power values for each of said display values.

9. The method of claim 8 wherein said display values include color Doppler values representing velocities of a moving substance.

10. The method of claim 9 further comprising the step of averaging said peak velocity over several cardiac cycles of said subject under examination using said method.

11. The method of claim 1 wherein said step of determining said optimum cardiac cycle of said living subject is comprised of the steps of:
   a. setting a threshold velocity;
   b. identifying each said peak velocity which exceeds said threshold to form a set of candidate peak velocities, and associating a time of occurrence of each said peak velocity with each of said set of candidate peak velocities;
   c. identifying discontinuities in said set of candidate peak velocities;
   d. locating a candidate peak velocity between said each of said discontinuities to form a set of peak systoles;
   e. determining a largest velocity of said set of peak systoles to determine a candidate peak systole;
   f. determining whether there is a second peak systole forward in time from said candidate peak systole;
   g. if there is not said second peak systole forward in time from said candidate peak systole then selecting a next largest velocity of said peak systoles, using said next largest velocity of said peak systoles as said candidate peak systole and repeating step f until there is a peak systole forward in time from said peak systole;
   h. if there is said second peak systole forward in time from said candidate peak systole, then locating a first minimum velocity which occurs before said candidate peak systole and identifying said first minimum velocity as an end diastole (ED) for said optimum cardiac cycle;
   i. locating a second minimum velocity which occurs before said second peak systole and identifying said second minimum velocity as a second end diastole (ED); and
   j. identifying a time period between said end diastole and said second end diastole as said optimum cardiac cycle.

12. The method of claim 11 wherein said step of performing said vascular measurements for said optimum cardiac cycle includes determining a minimum diastolic deflection (MDD) for said optimum cardiac cycle.

13. The method of claim 11 wherein said step of performing said vascular measurements for said optimum cardiac cycle includes determining a rise time for said optimum cardiac cycle.

14. The method of claim 13 wherein said step of performing said vascular measurements for said optimum cardiac cycle includes determining an acceleration index for said optimum cardiac cycle.

15. The method of claim 13 wherein said step of determining said rise time for said optimum cardiac cycle includes successively determining differences between pairs of adjacent peak velocities between said end diastole and said peak systole, and upon detecting a sign change between a first difference and a second difference, identifying a first adjacent peak velocity as a first systolic peak velocity for said optimum cardiac cycle.

16. The method of claim 15 wherein said step of determining said rise time for said optimum cardiac cycle includes determining a difference in time between said first systolic peak velocity and said end diastole.

17. The method of claim 15 further including the step of determining an acceleration index for said optimum cardiac cycle by determining a difference between said first systolic peak velocity and said end diastole divided by a difference in time between said first systolic peak velocity and said end diastole.

18. The method of claim 11 wherein said step of performing said vascular measurements for said optimum cardiac cycle includes determining a pulsatility index for said optimum cardiac cycle.

19. The method of claim 11 wherein said step of performing said vascular measurements for said optimum cardiac cycle includes determining a resistivity index for said optimum cardiac cycle.

20. An apparatus for making vascular measurements within a living subject in an ultrasonic system comprising:
   a. a first circuit for determining peak velocities of a spectra of echoes over a period of time due to pulses emitted into a subject under examination and storing said peak velocities into an array of peak velocities, said first circuit is further configured to divide said spectra into a plurality of regions to determine a threshold magnitude of said peak velocities and identify a first velocity that exceeds said threshold magnitude;
   b. a second circuit coupled to said first circuit for determining an optimum cardiac cycle for said subject under examination based upon said time series of said peak velocities; and
   c. a third circuit coupled to said second circuit for performing vascular measurements of said optimum cardiac cycle.

21. The apparatus of claim 20 further comprising a fourth circuit coupled to said first circuit for emitting said pulses into said subject under examination, receiving said echoes and determining Doppler frequency shifts from said pulses, and translating said Doppler frequency shifts to velocity information to form said spectra of echoes.

22. The apparatus of claim 20 wherein said first circuit includes:
   a. a division means for dividing said spectra in a plurality of regions according to ranges of said velocities;
   b. an averaging means coupled to said division means for determining an average magnitude of said velocity information for each of said plurality of regions;
   c. a minimum determination means coupled to said averaging means for determining a minimum magnitude of said average magnitudes for said plurality of regions;
   d. a threshold determination means coupled to said minimum determination means for determining a threshold magnitude of said peak velocities by adding a predetermined value to said minimum magnitude; and
   e. a thresholding means coupled to said threshold determination means for using said threshold magnitude to find a peak velocity by searching for said peak velocity from a Nyquist velocity of said spectra, identifying a first velocity which has an magnitude exceeding said threshold magnitude, and using said first velocity as said peak velocity.

23. The apparatus of claim 22 further comprising:
   a. an activation circuit for activating said division means, said averaging means, said minimum determination means, said threshold determination means, and said thresholding means on positive and negative velocities of said spectra; and
   b. a peak detection circuit coupled to said activation circuit for determining a greater absolute value of either a positive or a negative peak velocity and using said greater absolute value as said peak velocity.

24. The apparatus of claim 22 wherein said first circuit includes a signal processing circuit for determining a Doppler spectrum, performing a wall-filter on said spectrum, and determining a power estimate of said spectrum.

25. The apparatus of claim 22 further comprising an adjustment circuit for modifying a pulse repetition frequency (PRF) of said pulses if said peak velocity is at a Nyquist point in said spectra.

26. The apparatus of claim 22 further comprising a temporal averaging means coupled to said thresholding means for averaging said peak velocity over several cardiac cycles of said subject under examination.

27. The apparatus of claim 22 wherein said first circuit includes a input means for using display values for said ultrasonic system to determine said peak velocities, and power values for each of said display values.

28. The apparatus of claim 27 wherein said display values include color Doppler values representing velocities of a moving substance.

29. The apparatus of claim 28 further comprising a temporal averaging means coupled to said thresholding means for averaging said peak velocity over several cardiac cycles of said subject under examination.

30. The apparatus of claim 20 wherein said second circuit includes:
  a. a threshold determination means for setting a threshold velocity;
  b. a thresholding means coupled to said threshold determination means for identifying each said peak velocity which exceeds said threshold to form a set of candidate peak velocities which are stored in an array of candidate velocities, and associating a time of occurrence of each said peak velocity with each of said set of candidate peak velocities;
  c. an identification means coupled to said array of candidate velocities for identifying discontinuities in said set of candidate peak velocities; p1 d. a candidate peak detection means coupled to said identification means for locating a candidate peak velocity between said each of said discontinuities to form a set of peak systoles in an array of peak systoles;
  e. a largest velocity detection means coupled to said array of peak systoles for determining a largest velocity of said set of peak systoles to determine a candidate peak systole;
  f. a determining means coupled to said array of peak systoles for determining whether there is a second peak systole forward in time from said candidate peak systole and if there is not said second peak systole forward in time from said candidate peak systole then selecting a next largest velocity of said peak systoles, activating said largest velocity detection means for said next largest velocity of said peak systoles as said candidate peak systole until there is said second peak systole forward in time from said candidate peak systole;
  g. a minimum velocity detection means coupled to said array of peak velocities for locating a first minimum velocity which occurs before said candidate peak systole and identifying said first minimum velocity as an end diastole (ED) for said optimum cardiac cycle;
  h. a second minimum velocity detection means coupled to said array of peak velocities for locating a second minimum velocity which occurs before said second peak systole and identifying said second minimum velocity as a second end diastole (ED); and
  i. an optimum cardiac cycle identifying means coupled to said minimum velocity detection means and said second minimum velocity detection means for identifying a time period between said end diastole and said second end diastole as said optimum cardiac cycle.

31. The apparatus of claim 30 wherein said third circuit includes a minimum diastolic deflection determination circuit for determining a minimum diastolic deflection (MDD) for said optimum cardiac cycle.

32. The apparatus of claim 30 wherein said third circuit includes a rise time determination circuit for determining a rise time for said optimum cardiac cycle.

33. The apparatus of claim 32 wherein said third circuit includes an acceleration index determination means for determining an acceleration index for said optimum cardiac cycle.

34. The apparatus of claim 32 wherein said rise time determination circuit includes:
  a. successive determination means for successively determining differences between pairs of adjacent peak velocities between said end diastole and said peak systole; and
  b. a detection means coupled to said successive determination means for detecting a sign change between a first difference and a second difference, and identifying a first adjacent peak velocity as a first systolic peak velocity for said optimum cardiac cycle.

35. The apparatus of claim 34 wherein said rise time determination circuit further includes a difference circuit coupled to said detection means for determining a difference in time between said first systolic peak velocity and said end diastole.

36. The apparatus of claim 35 wherein said rise time determination circuit further includes an acceleration index determination circuit coupled to said detection means for determining an acceleration index for said optimum cardiac cycle by determining a difference between said first systolic peak velocity and said end diastole divided by a difference in time between said first systolic peak velocity and said end diastole.

37. The apparatus of claim 30 wherein said third circuit includes a pulsatility index determination means for determining a pulsatility index for said optimum cardiac cycle.

38. The apparatus of claim 30 wherein said third circuit includes a resistivity index determination means for determining a resistivity index for said optimum cardiac cycle.

39. A method in an ultrasonic system comprising the following steps:
  a. determining peak velocities of a spectra of echoes over a period of time due to pulses emitted into a subject under examination, determining said peak velocities further includes dividing said spectra into a plurality of regions to determine a threshold magnitude of said peak velocities and identifying a first velocity that exceeds said threshold magnitude; and
  b. based upon said peak velocities of said spectra over said period of time, determining a set of said peak velocities representing and optimum cardiac cycle for said subject under examination.

40. The method of claim 39 wherein said spectra are obtained by emitting said pulses into said subject under examination, receiving said echoes and determining Doppler frequency shifts from said pulses, and translating said Doppler frequency shifts to velocity information.

41. The method of claim 40 wherein said step of determining said peak velocities of said spectra comprises:
  a. dividing said spectra in a plurality of regions according to ranges of said velocity information;
  b. determining an average magnitude of said velocity information for each of said plurality of regions;

c. determining a minimum magnitude of said average magnitudes for said plurality of regions;

d. determining a threshold magnitude of said peak velocities by adding a predetermined value to said minimum magnitude; and e. using said threshold magnitude to find a peak velocity by searching for said peak velocity from a Nyquist velocity of said spectra, identifying a first velocity which has an magnitude exceeding said threshold magnitude, and using said first velocity as said peak velocity.

42. The method of claim 41 further comprising the step of repeating said steps a–e on positive and negative velocities of said spectra, determining a positive peak velocity, and a negative peak velocity, determining a greater absolute value of either said positive or said negative peak velocity and using said greater absolute value as said peak velocity.

43. The method of claim 42 wherein said step of determining said spectra comprises determining a Doppler spectrum, performing a wall-filter on said spectrum, and determining a power estimate of said spectrum.

44. The method of claim 43 further comprising the step of modifying a pulse repetition frequency (PRF) of said pulses if said peak velocity is at said Nyquist velocity in said spectra.

45. The method of claim 39 further comprising the step of averaging said peak velocity over several cardiac cycles of said subject under examination using said method.

46. The method of claim 39 wherein said step of determining said spectra comprises using display values for said ultrasonic system, and power values for each of said display values.

47. The method of claim 46 wherein said display values include color Doppler values representing velocities of a moving substance.

48. The method of claim 47 further comprising the step of averaging said peak velocity over several cardiac cycles of said subject under examination using said method.

49. An apparatus in an ultrasonic system comprising:

a. a first circuit for determining peak velocities of a spectra of echoes over a period of time due to pulses emitted into a subject under examination and storing said peak velocities into an array of peak velocities, said first circuit is further configured to divide said spectra into a plurality of regions to determine a threshold magnitude of said peak velocities and identify a first velocity that exceeds said threshold magnitude; and b. a second circuit coupled to said first circuit for determining an optimum cardiac cycle for said subject under examination based upon said time series of said peak velocities.

50. The apparatus of claim 49 further comprising a third circuit coupled to said first circuit for emitting said pulses into said subject under examination, receiving said echoes and determining Doppler frequency shifts from said pulses, and translating said Doppler frequency shifts to velocity information to form said spectra of echoes.

51. The apparatus of claim 50 further comprising an adjustment circuit for modifying a pulse repetition frequency (PRF) of said pulses if said peak velocity is at a Nyquist point in said spectra.

52. The apparatus of claim 49 wherein said first circuit includes:

a. a division means for dividing said spectra in a plurality of regions according to ranges of said velocities;

b. an averaging means coupled to said division means for determining an average magnitude of said velocity information for each of said plurality of regions;

c. a minimum determination means coupled to said averaging means for determining a minimum magnitude of said average magnitudes for said plurality of regions;

d. a threshold determination means coupled to said minimum determination means for determining a threshold magnitude of said peak velocities by adding a predetermined value to said minimum magnitude; and e. a thresholding means coupled to said threshold determination means for using said threshold magnitude to find a peak velocity by searching for said peak velocity from a Nyquist velocity of said spectra, identifying a first velocity which has an magnitude exceeding said threshold magnitude, and using said first velocity as said peak velocity.

53. The apparatus of claim 52 further comprising:

a. an activation circuit for activating said division means, said averaging means, said minimum determination means, said threshold determination means, and said thresholding means on positive and negative velocities of said spectra; and b. a peak detection circuit coupled to said activation circuit for determining a greater absolute value of either a positive or a negative peak velocity and using said greater absolute value as said peak velocity.

54. The apparatus of claim 52 wherein said first circuit includes a signal processing circuit for determining a Doppler spectrum, performing a wall-filter on said spectrum, and determining a power estimate of said spectrum.

55. The apparatus of claim 52 further comprising a temporal averaging means coupled to said thresholding means for averaging said peak velocity over several cardiac cycles of said subject under examination.

56. The apparatus of claim 52 wherein said first circuit includes a input means for using display values for said ultrasonic system to determine said peak velocities, and power values for each of said display values.

57. The apparatus of claim 56 wherein said display values include color Doppler values representing velocities of a moving substance.

58. The apparatus of claim 57 further comprising a temporal averaging means coupled to said thresholding means for averaging said peak velocity over several cardiac cycles of said subject under examination.

59. A method in an ultrasonic system of determining an optimum cardiac cycle comprising the following steps:

a. determining a time series of velocities over a period of time due to pulses emitted into a subject under examination;

b. identifying discontinuities in said time series of peak velocities which exceeds a threshold;

c. determining a candidate peak velocity between said each of said discontinuities to form a set of peak systoles;

d. determining a peak systole in said set of peak systoles which is followed by a second peak systole and which is preceded by a minimum peak velocity which occurs within a predetermined time before said peak systole and identifying said minimum peak velocity as an end diastole (ED);

e. locating a second minimum velocity which occurs before said second peak systole and identifying said second minimum velocity as a second end diastole (ED); and f. identifying a time period between said end diastole and said second end diastole as said optimum cardiac cycle.

60. The method of claim 59 further comprising the step of determining a minimum diastolic deflection (MDD) for said optimum cardiac cycle.

61. The method of claim 59 further comprising the step of determining a rise time for said optimum cardiac cycle.

62. The method of claim 61 further comprising the step of determining an acceleration index for said optimum cardiac cycle.

63. The method of claim 59 further comprising the step of determining a pulsatility index for said optimum cardiac cycle.

64. The method of claim 59 further comprising the step of determining a resistivity index for said optimum cardiac cycle.

65. The method of claim 64 further comprising the steps of successively determining differences between pairs of adjacent peak velocities between said end diastole and said peak systole, and upon detecting a sign change between a first difference and a second difference, identifying a first adjacent peak velocity as a first systolic peak velocity for said optimum cardiac cycle.

66. The method of claim 65 further comprising the step of determining a difference in time between said first systolic peak velocity and said end diastole.

67. The method of claim 65 further including the step of determining an acceleration index for said optimum cardiac cycle by determining a difference between said first systolic peak frequency and said end diastole divided by a difference in time between said first systolic peak velocity and said end diastole normalized by the transmit frequency.

68. An apparatus for determining an optimum cardiac cycle comprising:

a. an input means for determining a time series of velocities over a period of time due to pulses emitted into a subject under examination;

b. an identification means coupled to said input means for identifying discontinuities in said time series of peak velocities which exceeds a threshold;

c. a peak detection means coupled to said identification means for determining a peak velocity between said each of said discontinuities to form a set of peak systoles;

d. a determination means coupled to said peak detection means for determining a peak systole in said set of peak systoles which is followed by a second peak systole and which is preceded by a minimum peak velocity which occurs within a predetermined time before said peak systole and identifying said minimum peak velocity as an end diastole (ED);

e. a second minimum velocity detection means coupled to said determination means for locating a second minimum velocity which occurs before said second peak systole and identifying said second minimum velocity as a second end diastole (ED); and f. an optimum cardiac cycle identifying means coupled to said minimum velocity detection means for identifying a time period between said end diastole and said second end diastole as said optimum cardiac cycle.

69. The apparatus of claim 68 further comprising a minimum diastolic deflection determination circuit coupled to said optimum cardiac cycle identifying means for determining a minimum diastolic deflection (MDD) for said optimum cardiac cycle.

70. The apparatus of claim 68 further comprising a rise time determination means coupled to said optimum cardiac cycle identifying means for determining a rise time for said optimum cardiac cycle.

71. The apparatus of claim 70 wherein said rise time determination means includes:

a. successive determination means for successively determining differences between pairs of adjacent peak velocities between said end diastole and said peak systole; and b. a detection means coupled to said successive determination means for detecting a sign change between a first difference and a second difference, and identifying a first adjacent peak velocity as a first systolic peak velocity for said optimum cardiac cycle.

72. The apparatus of claim 71 wherein said rise time determination circuit further includes a difference circuit coupled to said detection means for determining a difference in time between said first systolic peak velocity and said end diastole.

73. The apparatus of claim 70 wherein said rise time determination means further includes an acceleration index determination circuit coupled to said detection means for determining an acceleration index for said optimum cardiac cycle by determining a difference between said first systolic peak frequency and said end diastole divided by a difference in time between said first systolic peak velocity and said end diastole and normalized by the transmit frequency.

74. The apparatus of claim 68 further comprising an acceleration index determination means coupled to said optimum cardiac cycle identifying means for determining an acceleration index for said optimum cardiac cycle.

75. The apparatus of claim 68 further comprising a pulsatility index determination means coupled to said optimum cardiac cycle identifying means for determining a pulsatility index for said optimum cardiac cycle.

76. The apparatus of claim 68 a resistivity index determination means for determining a resistivity index for said optimum cardiac cycle.

\* \* \* \* \*